United States Patent [19]

Bljumberg et al.

[11] 4,127,603

[45] Nov. 28, 1978

[54] METHOD OF PREPARING METHACRYLIC ACID

[76] Inventors: Erna A. Bljumberg, Leninsky prospekt, 57, kv. 10, Moscow; Gennady F. Vytnov, ulitsa Uritskogo, 10a, kv. 29, Dzerzhinsk Gorkovskoi oblasti; Oleg V. Isaev, ulitsa Parshina, 21, korpus 2, kv. 12, Moscow; Oleg V. Krylov, ulitsa Dm. Ulyanova, 4, korpus 2, kv. 371, Moscow; Sergei A. Maslov, Veshnyakovskaya ulitsa, 6, korpus 4, kv. 56, Moscow; Lia Y. Margolis, ulitsa Dm. Ulyanova, 1/61, kv. 186, Moscow; Alexandr P. Sineokov, ulitsa Tsiolkovskogo, 49a, kv. 121 Dzerzhinsk Gorkovskoi oblasti; Evgeny S. Smirnov, Leninsky prospekt, 83, kv. 366, Moscow; Levon A. Tavadian, ulitsa Charentsa, 4, kv. 43, Erevan; Nikolai M. Emanuel, Vorobievskoe shosse, 2b, kv. 44, Moscow; Kapitalina I. Grobova, Moskovskoe shosse, 15, kv. 85, Gorky; Valentina V. Krylova, ulitsa Uritskogo, 8a, kv. 29, Dzerzhinsk Gorkovskoi oblasti, all of U.S.S.R.

[21] Appl. No.: 769,117

[22] Filed: Feb. 16, 1977

[30] Foreign Application Priority Data

Feb. 20, 1976 [SU] U.S.S.R. .............................. 2325546

[51] Int. Cl.$^2$ .............................................. C07C 51/32
[52] U.S. Cl. .................................. 562/533; 260/604 R
[58] Field of Search ......................... 260/530 N, 604 R

[56] References Cited

FOREIGN PATENT DOCUMENTS

| | | | |
|---|---|---|---|
| 625,848 | 4/1963 | Belgium .............................. | 260/530 N |
| 1,468,363 | 12/1968 | Fed. Rep. of Germany ...... | 260/530 N |
| 43-9045 | 4/1968 | Japan .................................. | 260/530 N |

*Primary Examiner*—Vivian Garner
*Attorney, Agent, or Firm*—Lackenbach, Lilling & Siegel

[57] ABSTRACT

A method of preparing methacrylic acid, which comprises liquid-phase oxidation of alpha-methylacrolein with an oxygen-containing gas in a medium of an organic solvent at a temperature ranging from 50° to 100° C and under a pressure of from 1 to 50 atm in the presence of a heterogeneous catalyst such as borides, carbides or nitrides of elements pertaining to Groups IVB-VB of the periodic system, or aluminum boride, carbide or nitride and in the presence of a polymerization inhibitor, whereafter the desired product is separated from the resulting reaction mixture. The method according to the present invention makes it possible to produce methacrylic acid with a high selectivity (up to 86% as calculated for the reacted alpha-methylacrolein). Conversion degree of the starting aldehyde is as high as 55%. There is no formation of polymeric products during the oxidation process.

7 Claims, No Drawings

METHOD OF PREPARING METHACRYLIC ACID

The present invention relates to organic chemistry and, more specifically, to methods of preparing methacrylic acid which is useful for the production of polyesters.

Known in the art are numerous methods of the preparation of methacrylic acid by oxidation of alpha-methylacrolein with an oxygen-containing gas. These methods pertain substantially to processes of gas-phase oxidation and feature a low conversion degree per pass and a small output, thus they are commercially unacceptable.

Also known in the art is a method of preparing methacrylic acid by a liquid-phase oxidation of alpha-methylacrolein with an oxygen-containing gas in a medium of an organic solvent. In this case the process is usually conducted in the presence of homogeneous catalysts such as acetates of copper or nickel.

This method has a disadvantage residing in that the resulting product contains admixtures of the soluble catalyst, and therefore additional technological stages are necessary for the recovery and regeneration of the catalyst. Furthermore, as a result of partial polymerization of the starting and, mainly, of the final product, polymeric compounds are accumulated in the reaction mixture, that contaminate the desired product and decelerate the process. It should also be noted that the results achieved by this method are not satisfactorily reproducible, thus commercial realization of this method is rather doubtful.

Further known in the art is a method of preparing methacrylic acid by liquid-phase oxidation of alpha-methylacrolein with an oxygen-containing gas in a medium of an organic solvent in the presence of a heterogeneous catalyst such as $V_2O_5$ at a temperature within the range of from 50° to 100° C and under a pressure of from 1 to 50 atm, followed by isolation of the desired product.

This method features an insufficiently high selectivity of the formation of methacrylic acid, which does not exceed 55%. Furthermore, the oxidation process occurs with the formation of resinous polymerization products exerting an inhibiting effect upon the process. Upon repeated use of the heterogeneous catalyst, the rate of the alpha-methylacrolein oxidation reaction is substantially reduced.

It is an object of the present invention to provide a method of preparing methacrylic acid, which would make it possible to increase selectivity of the formation of the desired product.

It is another object of the present invention to provide a method of preparing methacrylic acid, which would make it possible to eliminate the formation of polymeric compounds.

These and other objects of the present invention are accomplished by a method of preparing methacrylic acid, which comprises liquid-phase oxidation of alpha-methylacrolein with an oxygen-containing gas in a medium of an organic solvent in the presence of a heterogeneous catalyst at a temperature ranging from 50° to 100° C and under a pressure of from 1 to 50 atm, followed by isolation of the desired product. In accordance with the present invention, the heterogeneous catalyst is made of borides, carbides, or nitrides of elements of Groups IVB–VB of the periodic system, or of aluminum, and the oxidation process is conducted in the presence of a polymerization inhibitor.

The method according to the present invention makes it possible to produce methacrylic acid with a selectivity of up to 86% as calculated for the reacted alpha-methylacrolein. Moreover, acetic acid is formed in the process as a by-product. Conversion of the starting aldehyde is as high as 55%. There is no formation of polymeric products in the course of the reaction. The starting alpha-methylacrolein is converted, at a substantially 100% selectivity, into valuable oxygen-containing products, i.e. methacrylic and acetic acids.

It is advisable that the catalyst and the polymerization inhibitor be used in amounts within the range of from 0.1 to 5% by weight of the starting reaction mixture, and within the range of from 0.00005 to 0.01% by weight of the starting reaction mixture respectively.

Among polymerization inhibitors use should be preferably made of a stable iminoxyl radical such as 2,2,6,6-tetramethyl-4-hydroxypiperidyl-1-oxyl.

The method according to the present invention stipulates oxidation of alpha-methylacrolein per se or alpha-methylacrolein incorporated into an oxidate produced by gas-phase oxidation of isobutylene with an oxygen-containing gas at a temperature ranging from 350° to 450° C in the presence of a heterogeneous oxide-type cobalt-molybdenum-bismuth-iron catalyst of the formula $Co_6Mo_{12}Bi_{0.8}Fe_{0.75}O_{45}$. Said oxidate is employed in the oxidation process without any additional treatment or purification thereof. Production of such an oxidate is now performed on a commercial scale.

In the method according to the present invention as the oxygen-containing gas use can be made of air, a mixture of oxygen with inert gases, or pure oxygen.

As the organic solvents use can be made, for example, of such solvents as benzene, acetone, tetrahydrofuran, acetonitrile.

As the polymerization inhibitors use can be made of copper dithiocarbamate, stable iminoxyl radicals such as 2,2,6,6-tetramethyl-4-hydroxypiperidyl-1-oxyl, 2,2,6,6-tetramethylpiperidyl-1-oxyl, and the like.

For a better understanding of the present invention the following specific examples illustrating the preparation of methacrylic acid are given hereinbelow.

EXAMPLE 1

Into an autoclave apparatus with a stainless steel reactor there are charged 5 ml (4.15 g) of alpha-methylacrolein 95 ml (76 g) of benzene, 0.1 g (0.12% by weight of the starting reaction mixture) of a powder-like tantalum boride, and 0.0005 g (0.00062% by weight of the starting reaction mixture of 2,2,6,6-tetramethyl-4-hydroxypiperidyl-1-oxyl. Into the reactor air is fed under a pressure of 15 atm, temperature in the apparatus is increased to 70° C, and then air is bubbled through the reactor at a rate of 10–12 l/hr with simultaneous stirring of the mixture by means of a magnetic stirrer. After 4 hours the process is discontinued. From the resulting reaction mixture there are separated, by way of rectification, 2.3g of methacrylic acid and alpha-methylacation, 2.3g of methacrylic acid and alpha-methylacrolein, g of acetic acid. Selectivity of the formation of acted alpha-methlacrolein, is 84% and 16% respectively. The degree of conversion of the starting aldehyde is 55%.

EXAMPLE 2

The oxidation process is conducted in a manner similar to that described in the foregoing Example 1, but under a pressure of 40 atm and at a temperature of 50° C. Charged into the reactor are 3.5 g of alpha-methylacrolein 95 ml (76 g) of benzene, 0.00005 g (0.00006% by weight) of 2,2,6,6-tetramethyl-4-hydroxypiperidyl-1-oxyl, and 0.1 g (0.12% by weight) of titanium boride. The process is discontinued after 5 hours. From the resulting reaction mixture 3.6 g of methacrylic acid and 0.96 g of acetic acid are isolated. Selectivity of the formation of methacrylic acid and acetic acid, as calculated for the reacted alpha-methylacrolein, is 86% and 14% respectively. The degree of conversion of the starting aldehyde is 41%.

EXAMPLE 3

The oxidation process is conducted in a manner similar to that described in the foregoing Example 1, but under a pressure of 5 atm and at a temperature of 70° C. Into the reactor there are charged 7 g of alpha-methylacrolein, 91 ml (73 g) of benzene, 0.0016 g (0.002% by weight) of 2,2,6,6-tetramethyl-4-hydroxypiperidyl-1-oxyl and 0.75 g (0.95% by weight) of titanium carbide. The process is discontinued after 4 hours. From the resulting reaction mixture 3.6 g of methacrylic acid and 0.96 g of acetic acid are isolated. Selectivity of the formation of methacrylic and acetic acids as calculated for the reacted alpha-methylacrolein is 84 and 16% respectively. The degree of conversion of the starting aldehyde is 50%.

EXAMPLE 4

The amounts of the starting components and the process conditions are the same as in Example 1 hereinbefore, except that as the catalyst use is made of titanium nitride in an amount of 0.12% by weight and the polymerization inhibitor is taken in an amount of 0.00005% by weight. The oxidation process is discontinued after 4 hours. From the resulting reaction mixture 2 g of methacrylic acid and 0.53 g acetic acid are separated. Selectivity of the formation of methacrylic and acetic acids is 84% and 16% respectively. The degree of conversion of the starting aldehyde is 49%.

EXAMPLE 5

The amounts of the starting components and the process conditions are the same as in Example 1 hereinbefore, except that as the catalyst use is made of aluminum boride in the amount of 0.25 g (3.0% by weight). After 3.5 hours the process is discontinued. From the resulting reaction mixture 2.2 g of methacrylic acid and 0.75 g of acetic acid are separated. Selectivity of the formation of methacrylic and acetic acids, as calculated for the reacted alpha-methylacrolein, is 80% and 20% respectively. The degree of conversion of the starting aldehyde is 55%.

EXAMPLE 6

The amounts of the starting components and the process conditions are the same as in the foregoing Example 1, except that as the catalyst use is made of aluminum nitride in the amount of 0.1 g (0.12% by weight). After 4 hours the process is discontinued. Selectivity of formation of methacrylic and acetic acids as calculated for the reacted alpha-methylacrolein is 81 and 19% respectively. The degree of conversion of the starting aldehyde is 54%.

EXAMPLE 7

The oxidation process is conducted in a manner similar to that described in Example 1 hereinbefore, except that as the catalyst use is made of niobium nitride in an amount of 5 g (6.0% by weight). The process is discontinued after 4 hours. Selectivity of the formation of methacrylic and acetic acids as calculated for the reacted alpha-acrolein is 81 and 18% respectively. The degree of conversion of the starting aldehyde is 48%.

EXAMPLE 8

The oxidation process is conducted in much the same manner as in Example 1 hereinbefore, except that as the catalyst use is made of niobium carbide in an amount of 0.04 g (0.05% by weight). The process of oxidation is stopped after 4.5 hours. Selectivity of the formation of methacrylic and acetic acids as calculated for the reacted alpha-methacrolein is 80 and 20% respectively. The degree of conversion of the starting aldehyde is 45%.

EXAMPLE 9

The oxidation process is conducted in a manner similar to that described in the foregoing Example 1, except that as the solvent use is made of acetone in an amount of 95 ml and as the catalyst — zirconium boride in an amount of 0.1% by weight, and the polymerization inhibitor is taken in an amount of 0.01% by weight. After 4 hours the oxidation process is discontinued. Selectivity of the formation of methacrylic acid and acetic acid as calculated for the reacted alpha-methylacrolein is 82 and 18% respectively. The degree of conversion of the starting aldehyde is 54%.

EXAMPLE 10

The oxidation process is conducted in much the same manner as in Example 1 hereinbefore, except that as the catalyst use is made of zirconium nitride in an amount of 0.1% by weight and as the solvent — acetone in an amount of 95 ml, and the process is conducted under the pressure of 50 atm. After 4 hours the process is discontinued. Selectivity of the formation of methacrylic and acetic acids as calculated for the reacted alpha-methylacrolein is 78 and 21% respectively. The degree of conversion of the starting aldehyde is 50%.

EXAMPLE 11

The oxidation process is conducted as in Example 1 hereinbefore, except that as the catalyst use is made of tantalum boride in an amount of 5% by weight and as the solvent — tetrahydrofuran in an amount of 95 ml, and as the oxygen-containing gas use is made of a mixture of nitrogen with oxygen (oxygen content in the mixture is 30 vol.%). After 3.5 hours the oxidation process is discontinued. Selectivity of the formation of methacrylic and acetic acids as calculated for the reacted alpha-methylacrolein is 75 and 25% respectively. The degree of conversion of the starting aldehyde is 55%.

EXAMPLE 12

The oxidation process is conducted as in Example 1 hereinbefore, except that as the solvent use is made of tetrahydrofuran in an amount of 95 ml and the process is carried out at the temperature of 100° C. After 2.5 hours the oxidation process is discontinued. Selectivity of the formation of methacrylic and acetic acids as calculated for the reacted alpha-methylacrolein is 70 and 26% respectively. The degree of conversion of the starting aldehyde is 54%.

EXAMPLE 13

The oxidation process is conducted in a manner similar to that described in Example 1 hereinbefore, except that as the catalyst use is made of aluminium carbide in the amount of 0.12% by weight, as the solvent use is made of acetonitrile in an amount of 95 ml; as the oxygen-containing gas — a mixture of nitrogen with oxygen (the content of oxygen in the mixture is 12% by volume). After 5 hours the process of oxidation is discontinued. Selectivity of formation of methacrylic and acetic acids as calculated for the reacted alpha-methylacrolein is 77 and 22% respectively. The degree of conversion of the starting aldehyde is 42%.

EXAMPLE 14

The oxidation process is conducted in much the same manner as in the foregoing Example 1, but under an air pressure of 1 atm. After 7 hours the oxidation process is discontinued. Selectivity of formation of methacrylic and acetic acids as calculated for the reacted alpha-methylacrolein is 70 and 28% respectively. The degree of conversion of the starting aldehyde is 26%.

EXAMPLE 15

The oxidation process is conducted in the manner described in the foregoing Example 1, except that as the polymerization inhibitor use is made of 2,2,6,6-tetramethylpiperidyl-1-oxyl in an amount of 0.00062% by weight. After 4 hours the oxidation process is discontinued. Selectivity of the formation of methacrylic and acetic acids as calculated for the reacted alpha-methylacrolein is 83 and 17% respectively. The degree of conversion of the starting aldehyde is 50%.

EXAMPLE 16

The oxidation process is conducted as in Example 1, except that as the polymerization inhibitor use is made of 2,2,6,6-tetramethylpiperidyl-1-oxyl in an amount of 0.000016 g (0.00002% by weight). After 4 hours the oxidation process is stopped. Selectivity of the formation of methacrylic and acetic acids as calculated for the reacted alpha-methylacrolein is 79 and 19% respectively. The degree of conversion of the starting aldehyde is 51%.

EXAMPLE 17

The oxidation process is conducted as in the foregoing Example 1, except that as the polymerization inhibitor use is made of copper dithiocarbamate in an amount of 0.024 g (0.03% by weight). After 4.5 hours the oxidation process is discontinued. Selectivity of the formation of methacrylic and acetic acids is 72 and 24 respectively, as calculated for the reacted alpha-methylacrolein. The degree of conversion of the starting aldehyde is 52%.

EXAMPLE 18

The oxidation process is conducted in a manner similar to that described in Example 1 hereinbefore, except that as the catalyst use is made of hafnium carbide in an amount of 0.12% by weight, and as the polymerization inhibitor use is made of copper dithiocarbamate in an amount of 0.00062% by weight. After 4 hours the oxidation process is discontinued. Selectivity of the formation of methacrylic and acetic acids is 69 and 27% respectively as calculated for the reacted alpha-methylacrolein. The degree of conversion of the starting aldehyde is 50%.

EXAMPLE 19

The oxidation process is conducted as in Example 1. 10 ml (9 g) of an oxidate produced by condensation of the off-gases from the process of oxidation of isobutylene, 90 ml (72 g) of benzene, 0.1 g (0.12% by weight) of titanium boride and 0.0005 g (0.00062% by weight) of 2,2,6,6-tetramethyl-4-hydroxypiperidyl-1-oxyl are charged into the reactor. The employed oxidate is produced by gas-phase oxidation of isobutylene by air at a temperature of 400° C in the presence of a heterogeneous oxide-type cobalt-molybdenum-bismuth-iron catalyst of the formula: $Co_6Mo_{12}Bi_{0.8}Fe_{0.75}O_{45}$. The oxidate has the following composition, per cent by weight: alpha-methylacrolein, 44; methacrylic acid, 12; acetic acid, 0.8; acetic aldehyde, 0.4; water, 41.8; non-identified impurities, 1% by weight. The resulting oxidate is employed in the process of oxidation of alpha-methylacrolein without any additional treatment or purification. After 4 hours the process of oxidation of alpha-methylacrolein is discontinued. From the resulting reaction mixture 2.95 g of methacrylic acid and 0.55 g of acetic acid are separated. Selectivity of the formation of methacrylic and acetic acids as calculated for the reacted alpha-methylacrolein is 84 and 16% respectively. The degree of conversion of alpha-methylacrolein is 45%.

What is claimed is:

1. A method of preparing methacrylic acid, comprising liquid-phase oxidation of alpha-methylacrolein with an oxygen-containing gas in a medium of an organic solvent at a temperature ranging from 50° to 100° C and under a pressure of 1 to 50 atm in the presence of a heterogeneous catalyst selected from the group consisting of borides, nitrides, and carbides of elements selected from the group consisting of aluminum and elements of Groups IVB–VB of the periodic system, in the presence of a polymerization inhibitor, followed by separation of the desired product from the reaction mixture resulting from the oxidation.

2. A method as claimed in claim 1, wherein the catalyst is employed in an amount of from 0.1 to 5% by weight of the starting reaction mixture.

3. A method as claimed in claim 1, wherein the polymerization inhibitor is used in an amount of from 0.00005 to 0.01% by weight of the starting reaction mixture.

4. A method as claimed in claim 1, wherein as the polymerization inhibitor use is made of a stable iminoxyl radical selected from the group consisting of 2,2,6,6-tetramethyl-4-hydroxypiperidyl-1-oxyl and 2,2,6,6-tetramethylpiperidyl-1-oxyl.

5. A method as claimed in claim 1, wherein as the polymerization inhibitor use is made of copper dithiocarbamate.

6. A method as claimed in claim 1, wherein alpha-methylacrolein is incorporated into an oxidate produced by gas-phase oxidation of isobutylene with an oxygen-containing gas at a temperature ranging from 350° to 450° in the presence of a heterogeneous oxidic cobalt-molybdenum-bismuth-iron catalyst of the formula:

$$Co_6Mo_{12}Bi_{0.8}Fe_{0.75}O_{45}.$$

7. A method as claimed in claim 1, wherein the organic solvent is selected from the group consisting of benzene, acetone, tetrahydrofuran, and acetonitrile.

* * * * *